United States Patent [19]
Cutler

[11] Patent Number: 5,900,230
[45] Date of Patent: * May 4, 1999

[54] DENTAL PRODUCTS TO TREAT AND PREVENT PERIODONTAL DISEASE

[75] Inventor: Edward T. Cutler, Merion, Pa.

[73] Assignee: Squigle, Inc., Narberth, Pa.

[*] Notice: This patent is subject to a terminal disclaimer.

[21] Appl. No.: 08/912,502

[22] Filed: Aug. 18, 1997

[51] Int. Cl.$^6$ ............... A61K 7/16; A61K 7/18; A61K 9/68; A61K 9/20
[52] U.S. Cl. ............... 424/49; 424/48; 424/435; 424/440; 424/52
[58] Field of Search ......................... 424/48–88

[56] References Cited

U.S. PATENT DOCUMENTS

| | | | |
|---|---|---|---|
| Re. 31,954 | 7/1985 | Fine et al. | 424/49 |
| 3,932,604 | 1/1976 | Barth | 424/49 |
| 3,970,747 | 7/1976 | Barth | 424/52 |
| 5,089,255 | 2/1992 | Gaffar et al. | 424/52 |
| 5,178,869 | 1/1993 | Ebine et al. | 424/401 |
| 5,256,402 | 10/1993 | Prencipe et al. | 424/53 |
| 5,376,360 | 12/1994 | Domke et al. | 424/52 |
| 5,424,059 | 6/1995 | Prencipe et al. | 424/52 |
| 5,496,541 | 3/1996 | Cutler | 424/50 |
| 5,531,982 | 7/1996 | Gaffar et al. | 424/49 |

FOREIGN PATENT DOCUMENTS

| | | |
|---|---|---|
| 1250807 | 3/1989 | Canada . |
| 138705 | 4/1985 | European Pat. Off. . |
| 251146 | 1/1988 | European Pat. Off. . |
| 405682 | 6/1990 | European Pat. Off. . |
| 2606533 | 8/1976 | Germany . |
| 760735 | 2/1976 | South Africa . |

OTHER PUBLICATIONS

H. Bleeg, "Nonspecific Cleavage of Collagen by Proteinases in the Presence of Sodium Dodecyl Sulfate," *Scand. J. Dent. Res.*, 98,235–241 (1990).

B. Herlofson, P. Barkvoll, "Sodium Lauryl Sulfate and Recurrent Aphthous Ulcers (a preliminary study)," *Acta Odontol. Scand.*, 52, 257–259 (1994). (Teaches to Avoid Sodium Lauryl Sulfate to Aviod Recurrent Aphthous Ulcers).

*Primary Examiner*—Shep K. Rose
*Attorney, Agent, or Firm*—Ronald W. Griffin

[57] ABSTRACT

The dental products of this invention can be used to treat and prevent periodontal disease. They contain a synergistic mixture of poloxamers, and/or poloxamer congeners, plus xylitol. These active ingredients are present in specific amounts. It is also necessary to eliminate all irritants from the dental products of this invention. The dental products of this invention include a dentifrice paste or gel, powder, granules, disintegrable tablet, and a mouthwash, lozenge, and chewing gum.

19 Claims, No Drawings

DENTAL PRODUCTS TO TREAT AND PREVENT PERIODONTAL DISEASE

The dental products of this invention can be used to treat and prevent periodontal disease. These dental products contain a synergistic mixture of poloxamers, and/or poloxamer congeners, plus xylitol. These active ingredients are present in specific amounts. It is also necessary to eliminate all irritants from the dental products of this invention.

BACKGROUND OF THE INVENTION

75% of the US population suffer from periodontal disease, also known as pyorrhea or gum disease. This epidemic costs billions of dollars a year and causes much pain, whether or not the disease is treated. And many of the people diagnosed with periodontal disease must endure draconian "maintenance therapy" three to four times a year for the rest of their lives.

According to the *Merck Manual* [$14^{th}$ ed., page 2104, R. Berkow, ed., Merck & Co., Rahway, N.J., 1982], the most common types of periodontal disease are gingivitis and periodontitis. Gingivitis (early stage gum disease) is an inflammation of the gingivae (gums), characterized by swelling, redness, change of normal contours, and bleeding. If gingivitis is allowed to progress, periodontitis (late stage gum disease), characterized by loss of tooth-supporting bone, will follow.

Again, according to the *Merck Manual*, the greatest single cause of periodontal disease is poor hygiene, indicated by the appearance of bacterial plaque and tartar (calcified plaque). It is felt that plaque and tartar are more sinister when they occur below the gum line than when they occur at or above the gum line. A well known periodontist has stated, "Plaque control is the alpha and omega of prevention, healing, and maintenance of periodontal health." [S. Ramfjord, *J. Clin. Periodontol.*, 14, 433 (1987)]

Daily brushing and flossing will prevent the majority of gum disease. But there still remain a number of unanswered questions:

1. Why do so many people practice poor oral hygiene?
2. Why do some people who practice good oral hygiene (including some periodontists) nonetheless contract periodontal disease?
3. Why do many of those who spend thousands of dollars on periodontal therapy subsequently practice poor oral hygiene?
4. Why do some maintenance phase periodontal patients, who faithfully practice good oral hygiene, continue to experience the ravages of periodontal disease?

The aim of this patent is to answer these questions, and thereby improve the lives of many people. The dental products of this invention represent a significant adjunct in the treatment and prevention of periodontal disease.

PRIOR ART

Relevant Poloxamer Patents

U.S. Pat. No. 2,773,801 (Dec. 11, 1956) describes a dentifrice containing poloxamer alone or poloxamer plus an anionic surfactant. Poloxamer consists of a block copolymer of ethylene oxide (EO) and propylene oxide (PO) arranged as $(EO)_a(PO)_b(EO)_a$ where the PO content ranges from 15 to 85 mole percent, the molecular weight ranges from 1,000 to 30,000, and the species is dispersible or soluble in water. Xylitol is not mentioned at all in the body of the patent nor in the claims.

U.S. Pat. No. 5,470,568 (Nov. 28, 1995) reveals the use of poloxamer as a membrane stabilizer to repair tissue damage resulting from cell membrane permeabilization suffered as a result of exposure to high energy radiation (x-rays, gamma rays, etc.), or from freezing and thawing (frostbite). Poloxamer congeners are also mentioned as having clinical efficacy. The benefits of using poloxamer or its congeners to treat or prevent periodontal disease are not mentioned, nor is the synergistic effect of xylitol plus poloxamer.

U.S. Pat. No. 5,494,660 (Feb. 27, 1996) reveals poloxamines (block copolymers of ethylene oxide (EO) and propylene oxide (PO) attached to and replacing the 4 amino hydrogens of ethylene diamine). Poloxamines are claimed to inhibit adhesion of microbes to biological surfaces, including teeth and oral mucosa (column 23, line 35 and column 25, paragraph 2). Nowhere in this patent is xylitol mentioned, nor its synergy with poloxamer or its congeners to treat or prevent periodontal disease.

The inventor's recent U.S. Pat. No. 5,496,541 (Mar. 5, 1996) reveals a totally nonirritating ternary surfactant system for dental products, and while it lists xylitol as an ingredient in its dental product examples, it does not mandate xylitol's presence in the invention's claims. Clinical studies performed after the patent was granted led to the realization of the unobvious synergy of xylitol plus poloxamer in the treatment and prevention of periodontal disease.

U.S. Pat. No. 5,605,687 (Feb. 25, 1997) reveals poloxamer and its congeners as substances which can reduce damage to electrically injured tissue by stabilizing cell membranes and reducing membrane permeability. The benefits of using poloxamer or its congeners to treat or prevent periodontal disease are not mentioned, nor is the synergistic effect of xylitol plus poloxamer.

Xylitol Toothpaste Patents

U.S. Pat. No. 3,932,604 (Jan. 13, 1976), describes a toothpaste containing 15 to 60% by weight of xylitol. Xylitol is cited as a noncariogenic sweetener which prevents plugging of the toothpaste tube neck if the tube is left uncapped overnight. The fact is omitted that xylitol profoundly inhibits the growth of dental plaque bacteria such as *Streptococcus mutans*. And the fact is omitted that it is the glycerin in toothpaste (not the xylitol) which prevents plugging of an open toothpaste tube when it is left uncapped overnight. No partiality is shown with respect to anionic, cationic, or nonionic surfactants. Poloxamers are mentioned as suitable nonionic surfactants, without recognizing the synergy of the xylitol-poloxamer combination with respect to treatment or prevention of periodontal disease. The claims do not mention any specific detergent.

ZA 760735 (Feb. 9, 1976), which is the same as U.S. Pat. No. DE 2,606,533 (Aug. 26, 1976), discloses dental products, containing at least 20 percent by weight of xylitol, to remineralize and prevent incipient caries. Poloxamer is not mentioned anywhere in the patent.

U.S. Pat. No. 3,970,747 (Jul. 20, 1976) differs from U.S. Pat. No. 3,932,604 only in its claims. U.S. Pat. No. 3,970,747 has more claims, including one for fluoride as an ingredient, but there is no more detail about surfactants in the claims. Example 5 of said patents cites a dentifrice containing 50% by weight of xylitol and 21% by weight of water, which together form a 71% solution of xylitol in water. However, the maximum solubility of xylitol in water at 25° C. is 66%. Thus, precipitation occurs within two hours after a 71% xylitol solution is cooled to 25° C.

U.S. Pat. No. 4,254,101 (Mar. 3, 1981) discloses a dentifrice containing 30 to 70 percent by weight of a humectant which could be xylitol, plus 0.03 to 1.0% of a carboxyvinyl polymer. Said toothpaste exhibits "excellent texture and . . . superior fluoride stability." Poloxamers are mentioned in the body of the patent as one possible surfactant among many. The claims list some specific anionic surfactants, but fail to mention poloxamers or their synergy with xylitol.

U.S. Pat. No. 4,314,990 (Feb. 9, 1982) discloses a dentifrice containing 30 to 70% by weight of a humectant which could be xylitol, plus a buffering agent. Said toothpaste exhibits "superior fluoride and flavor stability." Poloxamer is mentioned in the body of the patent as one possible surfactant among many. The claims list some specific anionic surfactants, but fail to mention poloxamers or their synergy with xylitol.

U.S. Pat. No. 4,383,987 (May 17, 1983) discloses a ternary surfactant system consisting of poloxamer plus xanthan gum plus high molecular weight polyethylene oxide. Xylitol is cited without special mention in a set of possible humectants in the body of the patent. But xylitol is not mentioned in the claims, although glycerin, sorbitol, and maltitol are. The object of the patent is to offer a nonirritating alternative to the irritating anionic surfactants found in conventional toothpaste. Said anionic surfactants can cause " . . . irritation in the oral cavity, mild bitterness, sloughing of some oral mucosa . . . ."

U.S. Pat. No. 4,407,788 (Oct. 4, 1983) discloses high molecular weight polyethylene oxide, which is supposed to beneficially flocculate the dentifrice polishing agent. Xylitol is cited once as a humectant, but not at all in the claims. Numerous surfactants are mentioned in body of the patent, but not at all in the claims. The only surfactants singled out for special attention are the salts of N-alkanoyl sarcosine, because they "exhibit a prolonged and marked effect in the inhibition of acid formation . . . in addition to exerting some reduction in the solubility of tooth enamel . . . ." The inventor fails to state that these compounds were withdrawn from US dentifrices in 1975 because of concerns over irritancy to oral mucosa.

EP 138,705 (Apr. 24, 1985), which is the same as CA 1,250,807 (Mar. 7, 1989), discloses a dentifrice containing a mixture of 5 to 50 percent by weight of xylitol plus 2,000 to 20,000 ppm fluoride. Said xylitol-fluoride mixture has a synergistic effect in preventing caries. Poloxamer is not mentioned anywhere in the patent.

EP 251,146 (Jan. 7, 1988) discloses dental products containing a synergistic ternary mixture of 100 to 10,000 ppm fluoride plus 0.01 to 2.0 percent by weight of zinc ions plus 0.1 to 10.0 percent by weight of xylitol. This mixture inhibits plaque formation and reduces the drop in oral pH experienced after sucrose ingestion. Poloxamer is not mentioned anywhere in the patent.

EP 405,682 (Jun. 26, 1990), which is the same as U.S. Pat. No. 5,089,255 (Feb. 18, 1992), discloses a dentifrice to remineralize incipient cavities, said dentifrice containing 10 to 20% by weight of xylitol plus 150 to 1800 ppm of fluoride ions. Numerous surfactants are mentioned in body of the patent, but not at all in the claims. The only surfactants singled out for special attention are the salts of N-alkanoyl sarcosine, because they "exhibit a prolonged and marked effect in the inhibition of acid formation . . . in addition to exerting some reduction in the solubility of tooth enamel . . . ." The inventors fail to state that these compounds were withdrawn from US dentifrices in 1975 because of concerns over irritancy to oral mucosa.

U.S. Pat. No. 5,424,059 (Jun. 13, 1995) discloses a dentifrice which inhibits the formation of plaque and caries, and reduces gingivitis. Said dentifrice contains xylitol plus a polychlorinated hydroxylated diphenyl ether known as triclosan. Numerous surfactants are mentioned in body of the patent, but not at all in the claims. The only surfactants singled out for special attention are the salts of N-alkanoyl sarcosine, because they "exhibit a prolonged and marked effect in the inhibition of acid formation . . . in addition to exerting some reduction in the solubility of tooth enamel . . . ." The inventors fail to state that these compounds were withdrawn from US dentifrices in 1975 because of concerns over irritancy to oral mucosa. Example 3 of said patent lists a dentifrice containing 40% by weight of xylitol and 25% by weight of water. Thus, the aqueous concentration of xylitol is 61% by weight—a solution which is stable at 25° C., but will precipitate at temperatures below 15° C.

U.S. Pat. No. 5,531,982 (Jul. 2, 1996) discloses dental products containing 0.1 to 40 percent by weight of xylitol plus 0.05 to 4 percent by weight of triclosan (a polychlorinated hydroxylated diphenyl ether) or its congeners. This binary mixture is supposed to inhibit plaque formation and reduce gingivitis and caries. Numerous surfactants are mentioned in body of the patent, but not at all in the claims. The only surfactants singled out for special attention are the salts of N-alkanoyl sarcosine, because they "exhibit a prolonged and marked effect in the inhibition of acid formation . . . in addition to exerting some reduction in the solubility of tooth enamel . . . ." The inventors fail to state that these compounds were withdrawn from US dentifrices in 1975 because of concerns over irritancy to oral mucosa.

Current Xylitol Toothpastes

For over 10 years, xylitol-containing toothpastes have been sold throughout Europe (the major market) and elsewhere. The most common xylitol concentration in current European toothpastes is 10 percent by weight. The most common surfactant is sodium lauryl sulfate (SLS). In fact, there is presently no commercial toothpaste containing at least 10 percent by weight of xylitol, plus a mild surfactant and no SLS.

SUMMARY OF THE INVENTION

This invention describes dental products which encourage people to maintain good oral hygiene—compliance as the dentists would say. These dental products are dentifrice powders, granules, disintegrable tablets, dentifrice pastes or gels, dentifrice lozenges, dentifrice chewing gums, and mouthwashes. The dental products of this invention stabilize cell membranes of oral mucosa, reduce chronic irritation of oral mucosa, and profoundly reduce plaque and tartar growth. They also improve gum color and consistency, reduce bleeding on probing, and reduce periodontal pocket depth.

The dental products of this invention are distinguished by employing poloxamers and/or their congeners as the sole or main surfactant (for example, see the inventor's U.S. Pat. No. 5,496,541 Mar. 5, 1996).

Poloxamer consists of a block copolymer of ethylene oxide (EO) and propylene oxide (PO) arranged as $(EO)_a(PO)_b(EO)_a$ wherein the PO content ranges from 15 to 85 mole percent, the molecular weight ranges from 1,000 to 30,000, and the species is dispersible or soluble in water.

A suitable poloxamer congener, having the generic name meroxapol, consists of $(PO)_a(EO)_b(PO)_a$ where a does not exceed 200, b does not exceed 200, the molecular weight ranges from 1,000 to 30,000, and the species is dispersible or soluble in water.

A suitable poloxamer congener consists of trimethylolpropane block copolymerized with EO and then PO, where each of the 3 branches contains not more than 200 EO moieties and not more than 200 PO moieties, the molecular weight ranges from 1,000 to moieties and not more than 200 PO moieties, the molecular weight ranges from 1,000 to 30,000, and the species is dispersible or soluble in water. A closely related version of this congener consists of trimethylolpropane block copolymerized with PO and then EO with the same restrictions.

A suitable poloxamer congener, having the generic name poloxamine, consists of ethylene diamine copolymerized with EO and then PO, where each of the four branches contains not more than 200 EO moieties and not more than 200 PO moieties, the molecular weight ranges from 1,000 to 30,000, and the species is dispersible or soluble in water. A closely related version of this congener consists of ethylene diamine block copolymerized with PO and then EO with the same restrictions.

Other suitable poloxamer congeners can be made by block copolymerizing two or more alkylene oxides selected from the group {EO, PO, RO}, where RO is any alkylene oxide having up to 10 carbon atoms, to an alkane having one or more reactive substituents selected from the group {—SH, —NH$_2$, —RNH, —OH, —X }, where —X is any other functional group capable of being alkylated by an alkylene oxide, where the total number of reactive substituents equals no more than 10, and the total number of copolymerized branches equals at least two.

Each copolymerized branch must contain not more than 200 EO moieties and not more than 200 PO moieties, the molecular weight of the entire molecule must range between 1,000 to 30,000, and the species must be dispersible or soluble in water. Not more than 10 copolymerized EO—PO branches may protrude from the central initiator molecule.

The dental products of this invention must contain no less than 10 weight percent of xylitol. Said dental products are also free of irritating detergents such as sodium lauryl sulfate (SLS), sodium N-lauroyl sarcosinate, etc. Said dental products are also free of irritating flavors and essential oils which contain significant quantities of phenol, thymol, carvacral, eucalyptol, etc. Said dental products are also free of harsh antimicrobials such as chlorhexidine, sanguinarine, triclosan, etc., which may irritate gums, induce excessive growth of plaque or tartar, stain teeth, adversely affect the sense of taste, or cause long term adverse systemic effects.

It is well known that exposure to xylitol, in the form of chewing gum or 10% xylitol toothpaste (the standard concentration in Europe), can significantly reduce plaque and tartar in the mouth. And it is well known that poloxamers are virtually nonirritating surfactants—they are even used in opthalmic products. What has not been realized until now is that synergistic effects can occur when dental products contain both substances together. Poloxamer concentration should be at least 0.01 weight percent, and preferably at least 1 weight percent. Xylitol concentration should be at least 10% (clinical efficacy drops below 10%), preferably at least 20%, and more preferably at least 30%. It is also necessary to eliminate all irritants from the dental product formulations—no irritating detergents nor flavors, no irritating tartar control agents (for example, pyrophosphates and polyphosphates). The resulting dental products will then have significant clinical efficacy when it comes to treatment and prevention of periodontal disease.

The mild, effective formulation of the dental products of this invention makes the mouths of many periodontal disease victims feel good—which encourages them to brush and floss daily. Thus, the reason some people fail to observe good oral hygiene is the hitherto unspoken distaste for and aversion to conventional toothpaste. Another factor to consider is the daily irritation of oral mucosa brought about by "proper" use of conventional toothpastes which contain irritating sodium lauryl sulfate (or other irritating detergents), irritating flavors or flavor concentrations, and irritating tartar control agents. See: H. Bleeg, *Scand. J. Dent. Res.*, 98, 235 (1990) and B. Herlofson, P. Barkvoll, *Acta Odontol. Scand.*, 52, 257 (1994). Once you remove all the irritants from toothpaste, you give the mouths of periodontal disease victims a chance to heal—and heal they do—aided by the membrane stabilizing properties of poloxamer and the plaque fighting properties of xylitol working in synergy. On the other hand, if long term users of the dental products of this invention are switched back to conventional toothpaste, they often regress. Thus, we now have some insight into why many people fail to carry out good oral hygiene, and why some people, in spite of following good oral hygiene regimens, still fall victim to periodontal disease.

DETAILED DESCRIPTION OF THE INVENTION AND ITS PREFERRED EMBODIMENTS

Dental products of this invention employ poloxamer and/or its congeners as the sole or main surfactant, wherein said surfactant comprises at least 0.01 weight percent, and preferably at least 1 weight percent of said dental product, and said dental product contains at least 10 weight percent, preferably at least 20 percent, and more preferably at least 30 percent of xylitol.

Toothpaste ES, formulated according to this invention, had the following composition:

| Ingredient | Description | Supplier | Weight Percent |
|---|---|---|---|
| Sylodent 15 | thickening silica | W. R. Grace | 9.00 |
| Sylodent 700 | abrasive silica | W. R. Grace | 7.00 |
| xylitol | | | 36.00 |
| distilled water | | | 33.82 |
| glycerin | | | 6.28 |
| Pluronic F127 | poloxamer | BASF | 4.00 |
| Aqualon 7MF | cellulose gum | Aqualon | 1.40 |
| Methocel K15M Premium | hydroxypropyl methylcellulose | Dow Chemical | 0.50 |
| favor | | | 1.00 |
| color | | | 0.75 |
| sodium fluoride | | | 0.24 |
| sodium hydroxide | | | 0.01 |
| TOTAL | | | 100.00 |

Periodontal patients using formulation ES experienced one or more of the following: less plaque and tartar, firmer and healthier looking gum tissue, reduced pocket depth, less bleeding on probing, greatly reduced canker sore recurrrence, and significantly reduced tooth sensitivity. And ES tasted so good that nearly all patients improved their oral hygiene (usually only 20% do). The following examples list the results.

EXAMPLE 1

Dr C is a periodontist with one patient who has improved since using ES toothpaste. Dr. C chose this patient because her gums were especially prone to ulceration. They no longer are.

EXAMPLE 2

Dr. F is a periodontist with one patient who has experienced significant plaque and tartar reduction since she began using ES toothpaste—and she brushes her teeth only once a day! Dr. F noted the improvement before he was informed that the patient was using formulation ES.

EXAMPLE 3

Dr. S is a periodontist with one patient who has improved since using ES toothpaste. Gum surgery has been indefinitely postponed, and maintenance visit intervals have been extended from 6 times annually to 4 times annually. Dr. S noted the improvement before he was informed that the patient was using formulation ES.

EXAMPLE 4

Dr. Z is a periodontist with 6 maintenance phase patients who have improved since using ES toothpaste and she has observed nearly 100% compliance with good oral hygiene in these patients—it is usually 20%. Here are the details of the tests which were performed:

TABLE 4A

Test: Plaque Index
Description: Visual estimate of the percent of tooth surfaces covered by plaque. Same observer for each patient.

| Patient | Length of Test (months) | Plaque Score | |
|---|---|---|---|
| 1 | 6 | initial: | 25 |
|   |   | final: | 10 |
|   |   | decrease: | 60% |
| 2 | 3 | initial: | 50 |
|   |   | final: | 25 |
|   |   | decrease: | 50% |
| 3 | 3 | initial: | 50 |
|   |   | final: | 25 |
|   |   | decrease: | 50% |
| 4 | 3 | initial: | 100 |
|   |   | initial: | 50 |
|   |   | decrease: | 50% |
| 5 | 6 | initial: | 100 |
|   |   | final: | 90 |
|   |   | decrease: | 10% |
| 6 | 1 | initial: | 100 |
|   |   | final: | 20 |
|   |   | decrease: | 80% |

TABLE 4B

Test: Bleeding on Probing
Description: Percent of bleeding areas found. All natural teeth were checked (6 positions per tooth). Same observer for each patient.

| Patient | Length of Test (months) | Bleeding on Probing | |
|---|---|---|---|
| 1 | 6 | initial: | 25 |
|   |   | final: | 0 |
|   |   | decrease: | 100% |
| 2 | 3 | initial: | 50 |
|   |   | final: | 25 |
|   |   | decrease: | 50% |
| 3 | 3 | initial: | 50 |
|   |   | final: | 25 |
|   |   | decrease: | 50% |
| 4 | 3 | initial: | 100 |
|   |   | final: | 50 |
|   |   | decrease: | 50% |

TABLE 4B-continued

Test: Bleeding on Probing
Description: Percent of bleeding areas found. All natural teeth were checked (6 positions per tooth). Same observer for each patient.

| Patient | Length of Test (months) | Bleeding on Probing | |
|---|---|---|---|
| 5 | 6 | initial: | 100 |
|   |   | final: | 90 |
|   |   | decrease: | 10% |
| 6 | 1 | initial: | 100 |
|   |   | final: | 20 |
|   |   | decrease: | 80% |

EXAMPLE 5

Dentifrice Powder, Granules, or Disintegrable Tablets

One of the embodiments of this invention is a periodontal disease preventing and treating powder to be slurried with water in the hand of the user, and brushed onto the user's teeth. A typical formula for a dentifrice powder according to this invention is:

| Ingredient | Weight % |
|---|---|
| calcium carbonate | 50.0 |
| xylitol | 31.0 |
| microcrystalline cellulose | 14.6 |
| Pluronic F127 | 2.0 |
| xanthan gum | 1.0 |
| Methocel K15M Premium | 0.5 |
| flavor | 0.9 |

If desired, the powder can be converted to granules and used for the same purpose, or the granules can be blended with 0.5% by weight of a tablet lubricant and compressed into a tablet which disintegrates in the mouth and can then be chewed into a paste.

EXAMPLE 6

Dentifrice Lozenge

One of the embodiments of this invention is a periodontal disease preventing and treating hard or soft lozenge to be sucked on by the user. A typical formula for a lozenge according to this invention is:

| Ingredient | Weight % |
|---|---|
| xylitol | 91.6 |
| Pluronic F127 | 4.0 |
| cellulose gum (Aqualon 7MF) | 1.0 |
| Methocel K15M Premium | 0.5 |
| calcium carbonate | 2.0 |
| flavor | 0.9 |

EXAMPLE 7

Dentifrice Chewing Gum

One of the embodiments of this invention is a periodontal disease preventing and treating chewing gum. A typical formula for a chewing gum according to this invention is:

| Ingredient | Weight % |
| --- | --- |
| xylitol | 67.5 |
| gum base | 20.0 |
| calcium carbonate | 5.0 |
| glycerin | 3.0 |
| Pluronic F127 | 2.0 |
| cellulose gum (Aqualon 7MF) | 1.1 |
| Methocel K15M Premium | 0.5 |
| flavor | 0.9 |

EXAMPLE 7

Mouthwash

One of the embodiments of this invention is a periodontal disease preventing and treating mouthwash. A typical formula for a mouthwash according to this invention is:

| Ingredient | Weight % |
| --- | --- |
| water | 65.49 |
| xylitol | 32.1 |
| Pluronic F127 | 1.0 |
| cellulose gum (Aqualon 7MF) | 0.24 |
| Methocel K15M Premium | 0.12 |
| flavor | 0.9 |
| preservative | 0.1 |
| sodium fluoride | 0.05 |

I claim:

1. A dental product to treat and prevent periodontal disease consisting essentially of:
   (A) not less than 0.01 weight percent of a poloxamer or poloxamer congener surfactant;
   (B) not less than 10 weight percent of xylitol; and as a proviso
   (C) said dental product being free of irritating detergents, including sodium lauryl sulfate and sodium N-lauroyl sarcosinate;
   (D) said dental product being also free of irritating flavors and essential oils, including phenol, thymol, carvacrol, and eucalyptol; and
   (E) said dental product being also free of irritating antimicrobials, including chlorhexidine, alexidine, cetylpyridinium chloride, benzalkonium chloride, benzethonium chloride, sanguinarine, and triclosan.

2. A dental product according to claim 1, wherein said poloxamer consists of a block copolymer of ethylene oxide and propylene oxide arranged as $(EO)_a(PO)_b(EO)_a$ where the PO content ranges from 15 to 85 mole percent, and the molecular weight ranges from 1,000 to 30,000.

3. A dental product according to claim 1, wherein said poloxamer congener, having the generic name meroxapol, consists of $(PO)_a(EO)_b(PO)_a$ where a does not exceed 200, b does not exceed 200, the molecular weight ranges from 1,000 to 30,000, and the species is dispersible or soluble in water.

4. A dental product according to claim 1, wherein said poloxamer congener consists of trimethylolpropane block copolymerized with EO and then PO (or vice versa), where each of the three branches contains not more than 200 EO moieties and not more than 200 PO moieties, the molecular weight ranges from 1,000 to 30,000, and the species is dispersible or soluble in water.

5. A dental product according to claim 1, wherein said poloxamer congener, having the generic name poloxamine, consists of ethylene diamine copolymerized with EO and then PO (or vice versa), where each of the four branches contains not more than 200 EO moieties and not more than 200 PO moieties, the molecular weight ranges from 1,000 to 30,000, and the species is dispersible or soluble in water.

6. A dental product according to claim 1, wherein said poloxamer congener is made by block copolymerizing two or more alkylene oxides selected from the group {EO, PO, RO}, where RO is any alkylene oxide having up to 10 carbon atoms, to an alkane having one or more reactive substituents selected from the group {—SH, —NH$_2$, —RNH, —OH, —X}, where —X is any other functional group capable of being alkylated by an alkylene oxide, where the total number of reactive substituents equals no more than 10, and the total number of copolymerized branches equals at least two.

7. A dental product according to claim 6, wherein each copolymerized branch must contain not more than 200 EO moieties and not more than 200 PO moieties, the molecular weight of the entire molecule must range between 1,000 to 30,000, the species must be dispersible or soluble in water, and not more than 10 copolymerized EO—PO branches may protrude from the central initiator molecule.

8. A dental product according to claim 1, wherein said dental product is selected from the group consisting of dentifrice powders, granules, disintegrable tablets, dentifrice pastes or gels, dentifrice lozenges, dentifrice gums, and mouthwashes.

9. A dental product according to claim 1, containing as secondary surfactants anionic polysaccharides and/or nonionic cellulose ethers, with no other secondary surfactants being allowed.

10. A dental product according to claim 9, wherein the anionic polysaccharide is selected from the group consisting of alginic acid, gum arabic, carrageenan, carboxymethyl cellulose, karaya gum, pectin, gum tragacanth, and xanthan gum.

11. A dental product according to claim 9, wherein the nonionic cellulose ether is selected from the group consisting of methyl cellulose, ethyl cellulose, hydroxyethyl cellulose, hydroxypropyl cellulose, and hydroxypropylmethyl cellulose.

12. A dental product according to claim 1, which is free of all irritating flavors and/or flavor concentrations.

13. A dental product according to claim 1, which is further free of all irritating antimicrobials.

14. A dental product according to claim 1, which is free of all foam suppressors selected from the group consisting of polyacrylates, sulfonated polyacrylate oligomers, polydimethylsiloxanes, azacycloalkane-2, 2-diphosphonic acids, synthetic polymeric carboxylates, and their congeners.

15. A dental product according to claim 1, further comprising:
   a. 5 to 60% by weight of polyol humectants selected from the group consisting of glycerin, mannitol, polyethylene glycol, and sorbitol; and
   b. 0.001 to 5% by weight of sweeteners selected from the group consisting of acesulfame, aspartame, dihydrochalcones, glycyrrhizin and its derivatives, raw and extracted licorice, saccharin, stevia and the rebaudosides, sucralose, and talin and the thaumatins.

16. A dental product according to claim 15, in the form of a dentifrice chewing gum containing 5 to 60% by weight of gum base selected from the group consisting of chicle and polybutenes.

17. A dental product according to claim 15, further comprising one or more of the following ingredients:

a. 1 to 60% by weight of a mild abrasive, having a hardness less than or equal to that of tooth enamel, selected from the group consisting of calcium carbonate, dibasic calcium phosphate, tribasic calcium phosphate, calcium pyrophosphate, and hydroxyapatite;

b. 1 to 60% by weight of a strong abrasive, having a hardness greater than that of tooth enamel, selected from the group consisting of alumina, silica, titania, and fluoroapatite;

c. 0.1 to 10% by weight of flavor;

d. 1 to 2000 ppm by weight of fluoride-containing compound selected from the group consisting of sodium fluoride and sodium monofluorophosphate;

e. 0.1 to 10% by weight of a mono-, di-, or polydentate acid or its salts selected from the group consisting of citric acid, ethylenediaminetetraacetic acid, ascorbic acid, and sulfuric acid to adjust and maintain the pH between 6 and 10;

f. 0.1 to 1.0% by weight of preservative selected from the group consisting of paraben, potassium sorbate, and calcium propionate;

g. 0.1 to 1.0% by weight of antioxidant selected from the group consisting of ascorbic acid, $\alpha$-tocopherol, $\beta$-carotene, coenzyme $Q_{10}$, and melatonin;

h. 5 to 95% by weight of water; and i. 0.1 to 10% by weight of a thickener, selected from the group consisting of colloidal cellulose, hydrated silica, polyethylene glycol, and polyvinylpyrrolidone.

18. A dental product according to claim 17, in the form of a dentifrice tablet, containing 0.1 to 1.0% by weight of a tablet lubricant selected from the group consisting of calcium stearate, magnesium stearate, hydrogenated vegetable oil, and beeswax.

19. A dental product according to claim 1, wherein care is taken to eliminate all irritants from the formulation.

* * * * *